Figure 1:
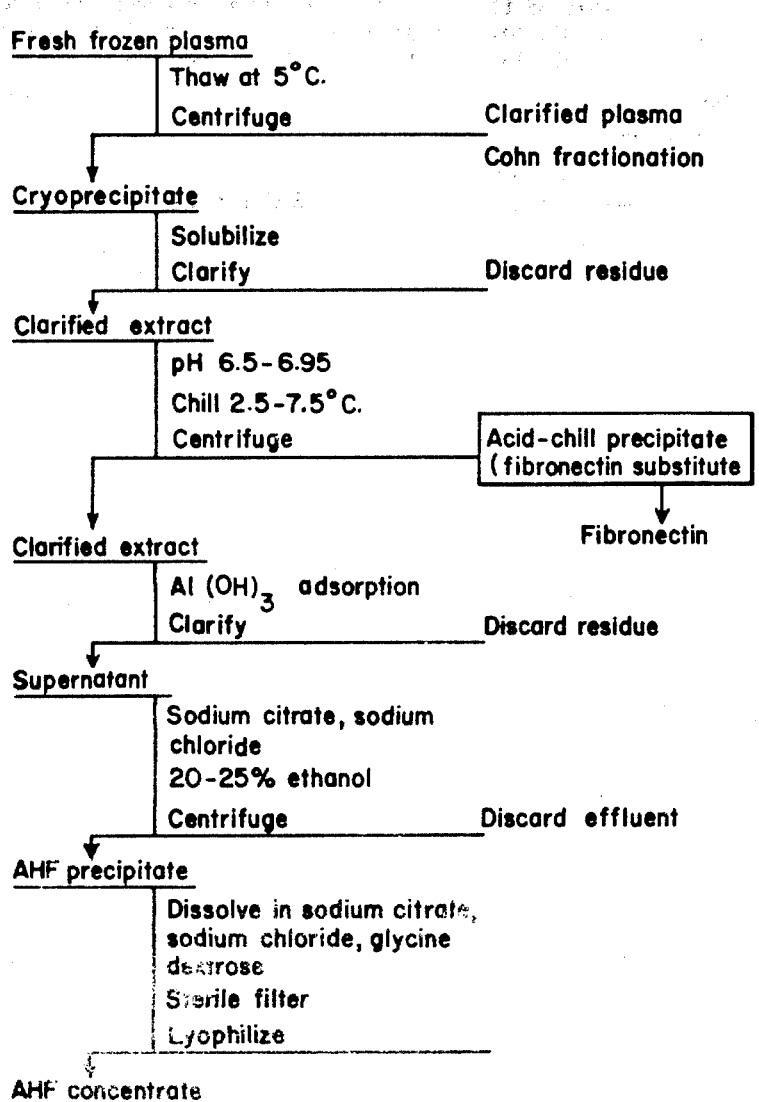

United States Patent [19]

Wallace et al.

[11] 4,455,300

[45] Jun. 19, 1984

[54] FIBRONECTIN COMPOSITIONS

[75] Inventors: Donald G. Wallace, Albany; Phillip M. Schneider, Alameda; John L. Lundblad, El Cerrito, all of Calif.

[73] Assignee: Cutter Laboratories, Inc., Berkeley, Calif.

[21] Appl. No.: 381,808

[22] Filed: May 25, 1982

Related U.S. Application Data

[63] Continuation of Ser. No. 127,340, Mar. 5, 1980, Pat. No. 4,341,764.

[51] Int. Cl.$^3$ .............................................. A61K 35/14
[52] U.S. Cl. ................................................... 424/101
[58] Field of Search ......................................... 424/101

[56] References Cited

U.S. PATENT DOCUMENTS 4,210,580  7/1980  Amrani ................................. 424/101
4,315,906  2/1982  Gelder ..................................... 424/9

PUBLICATIONS

Mori et al.-Chem. Abst. vol. 92 (1980) p. 90221z (article date 1979).
Vuento-Biochem. J. vol. 183 (1979) pp. 331-337.

Primary Examiner—Sam Rosen
Attorney, Agent, or Firm—David J. Aston; Lester E. Johnson; Theodore J. Leitereg

[57] ABSTRACT

Novel compositions containing fibronectin and methods of isolating these compositions and fibronectin itself from blood plasma are disclosed.

3 Claims, 2 Drawing Figures

FIBRONECTIN COMPOSITIONS

This application is a continuation of application Ser. No. 127,340, filed Mar. 5, 1980, now U.S. Pat. No. 4,341,764.

BACKGROUND OF THE INVENTION

This invention relates to and has as an object provision of novel materials having fibronectin-like activity, which are suitable for use as sources of fibronectin and as fibronectin substitutes and novel methods of making these materials.

The therapeutic value of fibronectin has been recognized by a number of workers. Fibronectin plays an important role in cellular adhesion, malignant transformation, reticuloendothelial system function, and embryonic differentiation (Yamada et al., Nature, 1978, Vol. 275, pages 179-184; Saba, Ann. Surg., Aug. 1978, pages 142-152; Scovill et al., The Journal of Trauma, 1976, Vol. 16, No. 11, pages 898-904; and Scovill et al., Ann. Surg., Oct. 1978, pages 521-529.

The fractionation of human blood plasma to produce an antihemophilic factor (AHF) concentrate (Factor VIII) is known: Hershgold et al., J. Lab. Clin. Med., 1966, Vol. 67, pages 23-32 and U.S. Pat. Nos. 3,973,002 and 4,170,639, hereinafter '002 and '639, respectively. In the Hershgold and '002 processes cryoprecipitate is recovered from thawed pools of fresh frozen human plasma at a temperature of about 2°-10° C. by centrifugation and dried and washed to remove soluble proteins, then, the cryoprecipitate is extracted with an aqueous buffer, and the pH of the extract is adjusted to about 6.5-7.5. The so-adjusted aqueous extract of AHF proteins is purified by contact with aluminum hydroxide. After purification the aqueous AHF extract is constituted with buffer and saline, and its pH is adjusted to within the range 6.50-6.95. The so-adjusted solution is freeze-dried to yield solid AHF concentrate.

In the '002 process cryoprecipitate is extracted in aqueous buffer, and the extract is purified by contact with aluminum hydroxide as described above. The purified extract is adjusted to pH 6.0"7.0 by addition of acid and then chilled to 2°-20° C. for a period of about 15-60 minutes. After centrifugation, the residue is discarded and the supernatant is treated as described above to obtain a solid AHF concentrate.

In the manufacture of an AHF concentrate, therefore, cryoprecipitate is solubilized in an aqueous medium and, the solution is acidified to pH 6.0-7.0 by the addition of a biologically-acceptable acid as known in the art. The solution then is chilled to a temperature of about 2°-20° C. and centrifuged. The supernatant is separated from a residue, called the acid-chill precipitate, which is discarded, and is treated with aluminum hydroxide to purify it. An AHF concentrate is recovered from the so-purified supernatant according to the known procedure outlined above, i.e., constitution of the supernatant with buffer, saline, and acid and freeze-drying the supernatant.

We have found that the above-described acid-chill precipitate, which heretofore has been discarded, has fibronectin-like activity and may be employed directly for therapeutic treatments as a fibronectin substitute. Alternatively, this precipitate may be treated to give substantially pure fibronectin. To this end the acid-chill precipitate is subjected to techniques known in the art for isolating fibronectin such as methods described by Engvall et al., Int. J. Cancer, Vol. 20, at page 2 (1977), by Molnar et al., in Biochemistry, Vol. 18, page 3909 (1979), and by Chen et al., Analytical Biochemistry, Vol. 79, pages 144-151 (1977) and by Mosesson et al., J. Biol. Chem., Vol. 245, No. 21, pages 5728-5736 (1970). The method of Engvall et al., wherein contact with a gelatin-Sepharose affinity medium is employed, is the preferred method for treatment of the acid-chill precipitate to give fibronectin (Sepharose=Sepharose ®).

It should be noted that fibronectin currently is isolated from blood plasma by the methods described in the above references. However, it is not known to prepare fibronectin by isolation from an acid-chill precipitate derived from blood plasma cryoprecipitate.

Basically, the aforementioned method for producing acid-chill precipitate with fibronectin-like activity and fibronectin itself may be summarized as follows (FIG. 1):

Cryoprecipitate is obtained from thawed frozen blood plasma and solubilized in an aqueous medium. The solution is acidified and chilled to a pH and a temperature and for a period of time sufficient to form an acid-chill precipitate. Preferably, the pH is adjusted to within the range of about 5.0-6.95, more preferably about 6.50-6.95, and the solution is chilled to a temperature of about 2.5°-7.5° C. The period for precipitate formation is generally about 15-60 minutes. The acid-chill precipitate that forms is separated from the solution and can be used directly as a fibronectin substitute or as a source of fibronectin. Either product can be freeze-dried by known methods or in the presence of about 1-20% carbohydrate.

The acid-chill precipitate having fibronectin activity is a composition which contains about 14-24% of fibronectin, about 75-85% of fibrinogen, and a minor proportion, about 1% of cryoprecipitate proteins such as albumin and gamma globulin and less than 28 units (per gram of total protein) of antihemophilic factor (Factor VIII) activity.

It is to be noted that this novel composition can be prepared by methods other than acid-chill precipitation of aqueous cryoprecipitate solutions. We have discovered that electrophoretic separation applied to an aqueous cryoprecipitate solution using, for example, a Harwell continuous electrophoretic separator (AERE Harwell, Oxfordshire, England) results in a fraction having the same composition and activity as the aforedescribed acid-chill precipitate. Molecular sieving of aqueous cryoprecipitate solutions also yields a fraction having the same composition and activity as the above composition. The use of molecular sieves for other separations is well-known in the art and conventional molecular sieving agents with a molecular weight separation range of 100,000 to 2,000,000, can be employed such as, for example, Sepharose CL-4B ® and Sepharose CL-6B ® (Pharmacia, Inc., Uppsala, Sweden), cross-linked argarose resins (BioRad Laboratories, Inc., Richmond, Ca.) and so forth.

Fibronectin isolated from acid-chill precipitate or its equivalent composition contains about 90-98% fibronectin and less than about 10% fibrinogen and gamma globulin and is substantially free of albumin and antihemophilic factor (Factor VIII) activity, i.e., contains less than 1% albumin and less than 5 units of AHF activity per gram of total protein.

Figure 2:
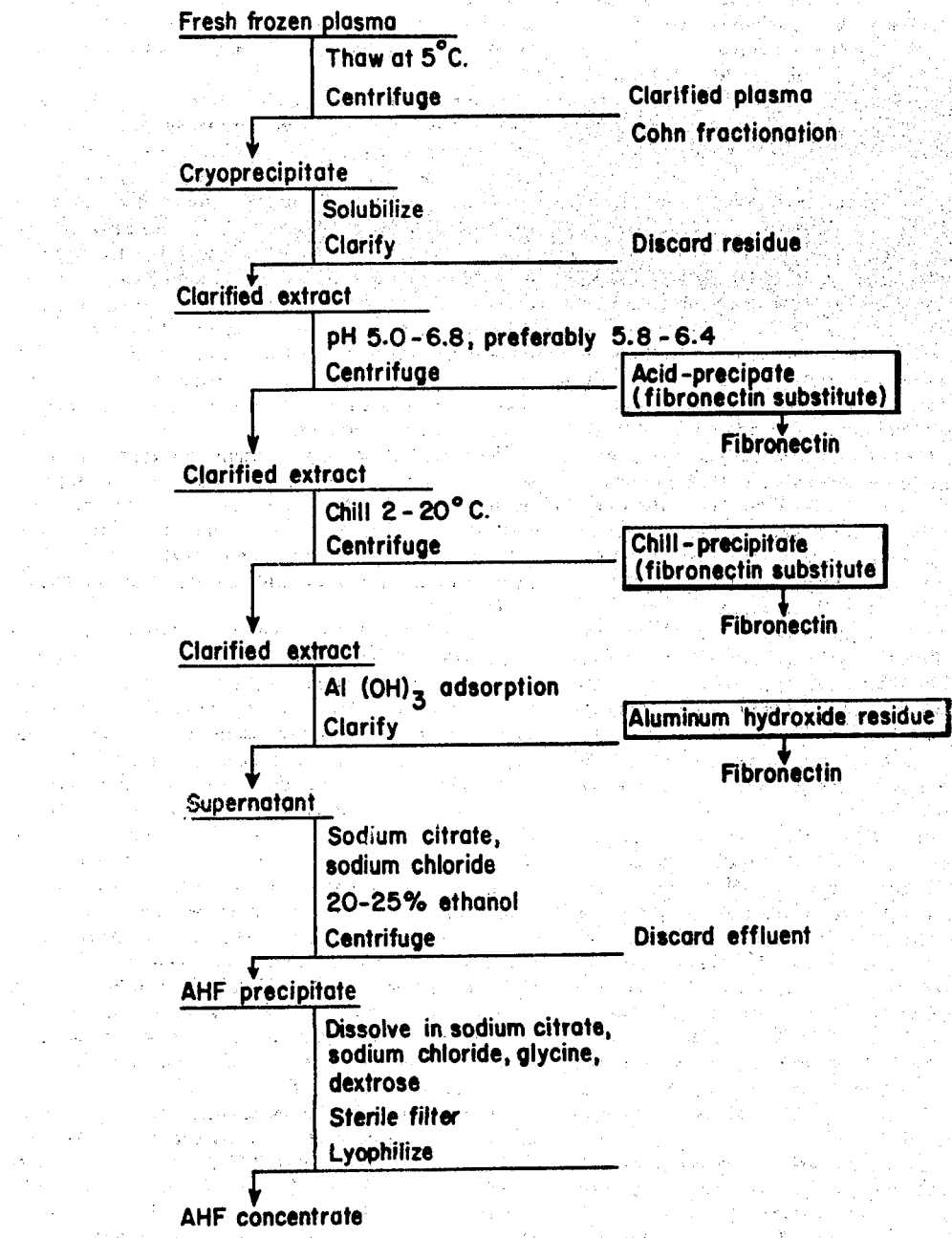

Other novel compositions with fibronectin-like activity and other sources of fibronectin are obtained according to the scheme outlined in FIG. 2. Cryoprecipitate is solubilized in an aqueous medium, preferably water, and the solution is acidified to a pH of about 5.0–6.8, preferably 5.8–6.4, as described above. The solution is centrifuged to give an acid-precipitate that is separated from the AHF solution. The acid-precipitate has fibronectin-like activity and may be used directly as a therapeutic agent in a manner similar to fibronectin. The acid-precipitate also may be treated to isolate fibronectin by the methods outlined above.

The AHF solution, after precipitation of the acid-precipitate, can be chilled to a temperature of about 2°–20° C., preferably 2.5°–7.5° C. and then centrifuged or the like to yield a chill-precipitate and an AHF supernatant. The chill-precipitate has substantially more fibronectin-like activity than either the acid-chill precipitate or the acid-precipitate. The chill-precipitate can be employed directly as a therapeutic agent in treating those medical disorders against which fibronectin is effective. Furthermore, fibronectin can be isolated from the chill-precipitate by application thereto of the aforedescribed methods.

The remaining AHF supernatant, after separation of chill-precipitate, is processed according to conventional procedures to produce an AHF concentrate. To this end the supernatant can be purified by contact with aluminum hydroxide and treated to remove water therefrom such as by lyophilization. The yield of AHF concentrate in the method of the invention is substantially the same as that obtained in the known processes for Factor VIII production.

The acid-precipitate fibronectin substance has the following composition: about 5–13% fibronectin, about 86–94% fibrinogen, about 1% cryoprecipitate proteins such as albumin and gamma globulin and is substantially free of Factor VIII activity, i.e., contains less than about 20 units Factor VIII activity per gram of total protein.

The chill-precipitate fibronectin substitute is a fibronectin-enriched material containing about 25–32% fibronectin, about 67–74% fibrinogen, about 1% cryoprecipitate proteins such as albumin and gamma globulin and is substantially free of Factor VIII activity, i.e., contains less than about 20 units Factor VIII activity per gram of total protein.

Fibronectin isolated from either the acid-precipitate or the chill-precipitate has substantially the same composition as that isolated from the acid-chill precipitate.

All of the above prepared materials may be processed according to known techniques such as sterile filtration, constitution with aqueous media conforming to physiological conditions of pH, saline, and the like, diafiltration, ultra-filtration, and lyophilization.

It is believed that the effectiveness of our novel compositions is due primarily to their fibronectin content. As mentioned above, however, these compositions have not been recognized in the art as having fibronectin-like activity. The acid-chill precipitate has been considered prior to our discovery to be a waste product and discarded. Furthermore, the aforementioned acid-precipitate and chill-precipitate heretofore have never been prepared. These compositions are now available with only slight modifications of the current process for preparing AHF concentrate and without diminishing the yield of AHF concentrate.

It is also within the scope of this aspect of the invention to isolate fibronectin from the aluminum hydroxide discard residue obtained in the purification of AHF solutions as described above either in conjunction with the acid, chill, or acid-chill steps outlined above or in the absence of any of those steps. The aluminum hydroxide residue is treated first to remove aluminum hydroxide therefrom such as by pH adjustment in an aqueous medium. The amphoteric nature of aluminum hydroxide renders it soluble in acid and basic medium. Consequently, the aluminum hydroxide residue is suspended in water and the pH is adjusted to either an acid or base level sufficient to dissolve the aluminum hydroxide but insufficient to dissolve or denature the biological proteins. A medically acceptable acid or base as known in the art may be used to carry out the pH adjustment. After dissolution of the aluminum hydroxide, the solution is separated by conventional means from the residue, which can be employed directly as a therapeutic agent or purified to give fibronectin by the methods outlined above.

It is important to note that the method of the invention for securing fibronectin and fibronectin substitutes from blood plasma is applied to cryoprecipitate by way of example and not limitation. In its broad ambit the method of the invention can be practiced on plasma fractions in general containing fibronectin and antihemophilic factor such as, for example, Cohn Fraction I paste. The plasma fraction is solubilized in aqueous medium. The solution is treated by the aforementioned methods to obtain a precipitate containing a major proportion of the fibronectin, i.e., greater than 50%, preferably greater than 60%, of the fibronectin, of the plasma fraction; and fibronectin is isolated from the precipitate as described above. Additionally, antihemophilic factor (Factor VIII) concentrate is isolated from the solution, which contains a substantial proportion of Factor VIII activity, i.e., greater than 50%, preferably greater than 80%, of the Factor VIII activity.

It is, of course, possible to isolate fibronectin directly from cryoprecipitate, Cohn Fraction I paste, cryoprecipitate wash solution, etc., by application of the known techniques thereto. However, in doing so one would lose an important benefit of the present invention, namely, production of an antihemophilic factor concentrate, in yields corresponding to those obtained in conventional Factor VIII production procedures.

In employing pasteurized fibronectin substitutes and pasteurized fibronectin itself for clinical (pharmaceutical) purposes, such as for intravenous administration to a patient, the fibronectin substitutes or fibronectin are reconstituted in sterile water. The aqueous mixture should contain a therapeutic amount of fibronectin, which may be defined as that amount of fibronectin having a curative or healing effect for the particular disorder being treated. Thus, for example, in the treatment of burns, a therapeutic amount of fibronectin would be that amount having a curative or healing effect on the burns. Similarly, if the fibronectin or fibronectin substitutes are administered to a cancer patient, the therapeutic amount would be that amount having a cancer curative or healing effect. The therapeutic amounts of fibronectin to be employed in a particular instance will be apparent to one skilled in the art. The sterile water may contain those materials generally recognized as approximating physiological conditions and/or as required by governmental regulation. Thus, the sterile water may contain a buffering agent to attain a physiologically acceptable pH. The sterile water may also contain sodium chloride and other physiologically necessary substances in physiologically acceptable amounts. In general, the material for intravenous administration should conform to regulations established by the Food and Drug Administration, which are available to those in the field.

The above aspects of the invention are illustrated further by the following examples.

EXAMPLE 1

Preparation of Fibronectin from Acid-Chill Precipitate

A modified method of Hershgold et al., supra, was followed to obtain cryoprecipitate. Fresh frozen human plasma was thawed at not more than 5° C. and warmed to not more than 15° C. The so-warmed plasma was chilled to 2° C. After 3 hours insoluble cryoprecipitate was collected by centrifugation at not more than 10° C.

Cryoprecipitate (1 kg.) was diced and suspended in 10 l. of sterile water at 32° C. for not more than 2 hours. Then, the mixture was adjusted to pH 6.8 by addition of 0.1 N hydrochloric acid and was chilled to 5° C. Precipitate (acid-chill precipitate) was removed by centrifugation at 5° C.

Acid-chill precipitate (1 kg. containing 260 g. of protein) from above was suspended in 13 l. of a 0.05 M sodium phosphate buffer (pH 7.6) containing 0.1 M sodium chloride (Buffer A). The suspension was clarified by filtration. A gelatin-Sepharose complex was prepared by covalently linking porcine gelatin to Sepharose CL-4B. To this end 24 g. of porcine gelatin was mixed with 1.2 kg. of Sepharose CL-4B, which had been activated with 60 g. of cyanogen bromide. The mixture was stirred at 5° C. for 16 hours and washed exhaustively with 4 M NaCl. The coupled Sepharose was stored in 4 M NaCl, and immediately before use it was equilibrated with Buffer A. The cyanogen bromide activation and protein coupling steps have been described by Cuatrecasas et al., (1968) Proc. Natl. Acad. Sci. U.S., Vol. 61, pages 636-643.

The clarified acid-chill precipitate suspension was stirred with 1.2 kg. of the above-prepared gelatin-Sepharose for 3 hours. The mixture was placed in a Büchner filtration funnel and washed with 30.6 liters of 1 M urea to remove unwanted proteins. Then, the mixture was washed with 3.6 l. of 4 M urea to elute fibronectin.

To remove urea the fibronectin-urea eluate was diafiltered (using an Amicon® hollow fiber membrane cartridge with a nominal retention of 10,000 molecular weight against Buffer A in 10% sucrose (0.1 g/ml)) after addition of sucrose to 10%.

The retentate was analyzed for fibronectin content by gel electrophoresis on unreduced and reduced sodium dodecylsulfate (SDS) polyacrylamide gel. The fibronectin band accounted for greater than 90% of the protein visible on the gel. The molecular weight of the fibronectin on unreduced SDS polyacrylamide gel was 400,000-500,000; the reported molecular weight is 450,000-500,000 by Yamada et al., Nature, 1978, Vol. 275, page 179. The molecular weight of the fibronectin on reduced SDS polyacrylamide gel was 250,000-270,000; the reported value is 210,000-250,000 by Yamada et al., supra.

The fibronectin was identified further by its amino acid composition, which agreed with that reported by Yamada et al., Biochemistry, 1977, Vol. 16, page 5552.

An antibody to the above-prepared purified fibronectin was prepared and it cross-reacted with commercially available fibronectin (Collaboration Research, Inc., Waltham, Mass.). In immunodiffusion studies the above-prepared fibronectin showed a line of identity with the commercial fibronectin when both samples were cross-reacted against the above antibody.

The above-prepared fibronectin was demonstrated to be greater than 95% pure as determined by stained SDS polyacrylamide gels.

The activity of the fibronectin was determined by the following assays:

Rat Liver Slice Assay described by Molnar et al. in Biochemistry, Vol. 18, page 3909 (1979). The assay was performed in scintillation vials with 2 to 16 µg. of added fibronectin, 10 units of heparin, gelatin-coated latex particles labeled with $^{125}I$ (10,000 cpm added to each vial), Krebs-Ringer buffer to a final volume of 1.2 ml., and a 100-150 mg. slice of fresh rat liver. This mixture was incubated for 30 minutes at 30°-37° C. with shaking. Uptake of labeled gelatin-latex, was enhanced up to 10 fold by fibronectin.

Agglutination Assay described by Check et al. in the J. Reticuloendothelial Soc., Vol. 25, pages 351-362 (1979). The assay was performed in a manner similar to the liver slice assay. Fibronectin (2 to 31 µg., sometimes up to 600 µg.) was added to vials containing 10 units of heparin, 300 µl. of a 0.6% solution of unlabeled gelatin-coated latex, and Krebs-Ringer buffer to a final volume of 1.2 ml. Vials were shaken for 30 minutes at 30°-37° C. Agglutination was scored visually by noting a transition from a milky solution to a clear solution with clumped particles. Activities are expressed as the lowest added amount of fibronectin at which agglutination occurred.

Rat liver slice assay showed activities of the fibronectin prepared in accordance with the invention to be about 2000-6000 units/mg. (Molnar et al., supra, reported 1300-2000 units/mg. for their fibronectin).

Agglutination activities were compared with the rat liver slice activities with good correlation. Generally, the agglutination activities were about 6-12 µg (fibronectin with an agglutination activity greater than 100 µg would be considered to be weakly active.

EXAMPLE 2

Preparation of Material with Composition Substantially the Same as Acid-Chill Precipitate Using a Harwell Electrophoresis Device Cryoprecipitate (140 g.) was prepared by a procedure described in Example 1 and was added to 2300 ml. of an aqueous solution containing TRIS-citrate buffer (pH 7.5). The protein concentration of the so-prepared solution was 15.3 mg/ml. and the specific conductance of the solution was 1-2 milli mho (m mho) per cm. (TRIS= Tris(hydroxymethyl)aminomethane).

The solution was passed through a Harwell continuous electrophoretic separator at a flow rate of 500 ml/min. Thirty fractions were collected. Fractions were initally analyzed by optical density at 280 nm for protein and for AHF procoagulant activity by the one stage method. By optical density two major peaks, one including fractions 6-15 and the other, fractions 16-21, were observed. These fractions were bulked into three pools, comprising fractions 2-11, 12-15, and 16-20. These pools were assayed for fibronectin on reduced SDS polyacrylamide gels.

The pool from fractions 12-15 had the following composition: 15% fibronectin, 84% fibrinogen, about 1% albumin and gamma globulin, and Factor VIII activity of about 64 units per g. of total protein.

EXAMPLE 3

Preparation of Material with Composition Substantially the Same as Acid-Chill Precipitate Using a Molecular Sieve A 64 l. capacity Stack Column ® manufactured by Pharmacia Corp. (Uppsala, Sweden) was packed with 80 l. Sepharose CL-4B ®. The Sepharose was equilibrated with a buffer solution containing 0.05 M sodium phosphate, 0.1 M sodium chloride at a pH of 7.6.

A solution of cryoprecipitate was prepared by a procedure the same as described in Example 1 and had a protein concentration of 20 mg/ml. Two liters of this solution were loaded onto the above-prepared column by a peristaltic pump. The column was eluted with the aforementioned buffer and 100-1 l. fractions were collected. Three peaks were detected by analysis of protein optical density at 280 nanometers (nm). The second peak (30 g. of protein) had the following composition: 15% fibronectin, 84% fibrinogen, 1% albumin and gamma globulin, and a Factor VIII activity of about 28 units per g. of total protein.

Having thus described the invention, what is claimed is:

1. A therapeutic composition, prepared from frozen human plasma, comprising: 14%-24% fibronectin, 75%-85% fibrinogen, andd about 1% cryoprecipitate proteins, and having less than 28 units per gram total protein of antihemophilic factor.

2. A therapeutic composition, prepared from frozen human plasma, comprising: about 5-13% fibronectin, about 86-94% fibrinogen, and about 1% cryoprecipitate proteins, and less that 20 units antihemophilic factor activity per gram total protein.

3. A therapeutic composition, prepared from frozen human plasma, comprising: about 25-32% fibronectin, about 67-74% fibrinogen, about 1% cryoprecipitate proteins and less than 20 units of antihemophilic factor per gram total protein.

* * * * *